US00PP21174P3

(12) United States Plant Patent
Skelton

(10) Patent No.: US PP21,174 P3
(45) Date of Patent: Jul. 27, 2010

(54) KIWIFRUIT PLANT NAMED 'Y374'
(50) Latin Name: *Actinidia chinensis*
Varietal Denomination: Y374

(75) Inventor: Donald Alfred Skelton, Huntly (NZ)
(73) Assignee: JB IP Ltd., Hastings (NZ)

( * ) Notice: Subject to any disclaimer, the term of this patent is extended or adjusted under 35 U.S.C. 154(b) by 0 days.
(21) Appl. No.: 12/284,744
(22) Filed: Sep. 24, 2008
(65) Prior Publication Data
US 2009/0235398 P1 Sep. 17, 2009
Related U.S. Application Data
(60) Provisional application No. 61/069,212, filed on Mar. 12, 2008.
(51) Int. Cl.
*A01H 5/00* (2006.01)
(52) U.S. Cl. ..... Plt./156
(58) Field of Classification Search ..... Plt./156
See application file for complete search history.

(56) References Cited

U.S. PATENT DOCUMENTS

PP11,066 P 9/1999 Lowe et al.
2008/0184401 P1 7/2008 Skelton

*Primary Examiner*—June Hwu
(74) *Attorney, Agent, or Firm*—Knobbe, Martens, Olson & Bear LLP

(57) ABSTRACT

A new and distinct kiwifruit variety is disclosed. The variety results from selection among a population of seedlings derived from crossing the kiwifruit selections known as 'A17' (not patented) and 'R4' (not patented). The fruit of the plant of this new kiwifruit variety is characterized by its internal medium-yellow color. The new kiwifruit variety has been named 'Y374.'

6 Drawing Sheets

Latin name of the genus and species of the plant claimed: *Actinidia chinensis.*

Variety denomination: 'Y374'.

BACKGROUND AND SUMMARY OF THE INVENTION

The invention relates to the discovery and asexual propagation of a new and distinct variety of kiwifruit, *Actinidia chinensis* 'Y374', as herein described and illustrated. The new kiwifruit variety 'Y374' was selected from a population of seedlings derived from crossing two kiwifruit selections A17 (unpatented), the female, and R4 (unpatented), the non-fruiting male, using controlled pollination in the course of a planned kiwifruit variety breeding program. The cross was made in October 1999 by Donald Alfred Skelton at Rangiriri, New Zealand.

The new kiwifruit variety 'Y374' may be distinguished from its parent, A17, in that A17 has flat sided fruit, while the fruit of 'Y374' is rounded, A17 has a strongly sharp protruding stylar end, while the fruit of 'Y374' has a rounded to slightly blunt protruding stylar end, and A17's fruit matures late in the season, while the fruit of 'Y374' matures medium early (i.e., late March to May in New Zealand). The new kiwifruit variety 'Y374' may be distinguished from its parent, R4, in that R4 is a non-fruiting male while 'Y374' is a fruit-bearing female. In addition, R4 has bark of a Greyed-green color (RHS 193B), while 'Y374' has bark colored Grey-brown (RHS 199B). The new kiwifruit variety 'Y374' may be distinguished from presenhtly available cultivars such as, for example, *Actinidia chinenis* variety 'Hort16A' (U.S. Plant Pat. No. 11,066), by the following distinguishing characteristics: the fruit of the new kiwifruit variety 'Y374' matures earlier than the fruit of 'Hort16A', and the fruir of the new kiwifruit variety 'Y374' expresses a medium-yellow flesh color.

The new kiwifruit variety 'Y374' may be distinguished from other presently available kiwifruit varieties featuring medium-yellow flesh fruit such as, for example, 'Y363' (unpatented), 'D15' (unpatented), 'X273' (unpatented), and 'Skelton A19' (unpatented), by the following distinguishing characteristics: the fruit shape of the new variety 'Y374' is obovoid compared with that of 'Y363', which is oblong. The fruit size of the new variety 'Y374' is large compared with that of 'D15', which is medium, and 'X273', which is small. Furthermore, the beak of the new variety 'Y374' is very small compared with that of 'Skelton A19', which is apparent.

Asexual propagation of the new kiwifruit variety 'Y374' by grafting, in Rangiriri, New Zealand, shows that the unique combination of characteristics of the variety come true to form and are established and transmitted through succeeding propagation. In order to obtain true-to-type clones of the initial plant, asexually propagated plants were obtained by grafting dormant buds from the original seedling onto *Actinidia chinensis* and *Actinidia deliciosa* rootstocks.

BRIEF DESCRIPTION OF THE FIGURES

The accompanying photographs illustrate in full color typical specimens of the fruit, flowers, and leaves of the new variety 'Y374'. The colors as depicted are as nearly true as is reasonably possible in a color representation of this type.

DETAILED BOTANICAL DESCRIPTION OF THE INVENTION

The following is a detailed description of the new variety. The specimens described were grown at Rangiriri, New Zealand. The observations were made in the 2005 to 2008 seasons on vines grafted onto *Chinensis* and *Deliciosa* rootstocks, and managed under standard orchard practice. Random measurements of each characteristic were obtained from samples of 6 plants unless otherwise stated.

Horticultural terminology is used in accordance with UPOV guidelines for kiwi. All dimensions are in millimeters, and all weights are in grams (unless otherwise stated). Certain characteristics of this variety, such as growth and color, may change with changing environmental conditions (e.g., light, temperature, moisture), nutrient availability, rootstocks, or other factors. Color descriptions and other terminology are used in accordance with their ordinary dictionary descriptions, unless the context clearly indicates otherwise. Color names beginning with a capital letter designate values based upon the R.H.S. Colour Chart published by the Royal Horticultural Society, London, England.

PLANT AND FOLIAGE

The plant is a female plant that expresses a twining habit of medium vigor. The average plant size in height and spread is 6 feet high and 6 feet square.

Tomentose hairs are absent from the young shoot. Anthocyanin coloration of the growing tip is not present.

The stem of the plant is smooth bark and colored Greyed-orange (RHS 176B) on the upper side. Hairs are absent from the plant stem. The lenticels are medium in number. The size of the bud support is large. The leaf scar is deep.

Figure 5:
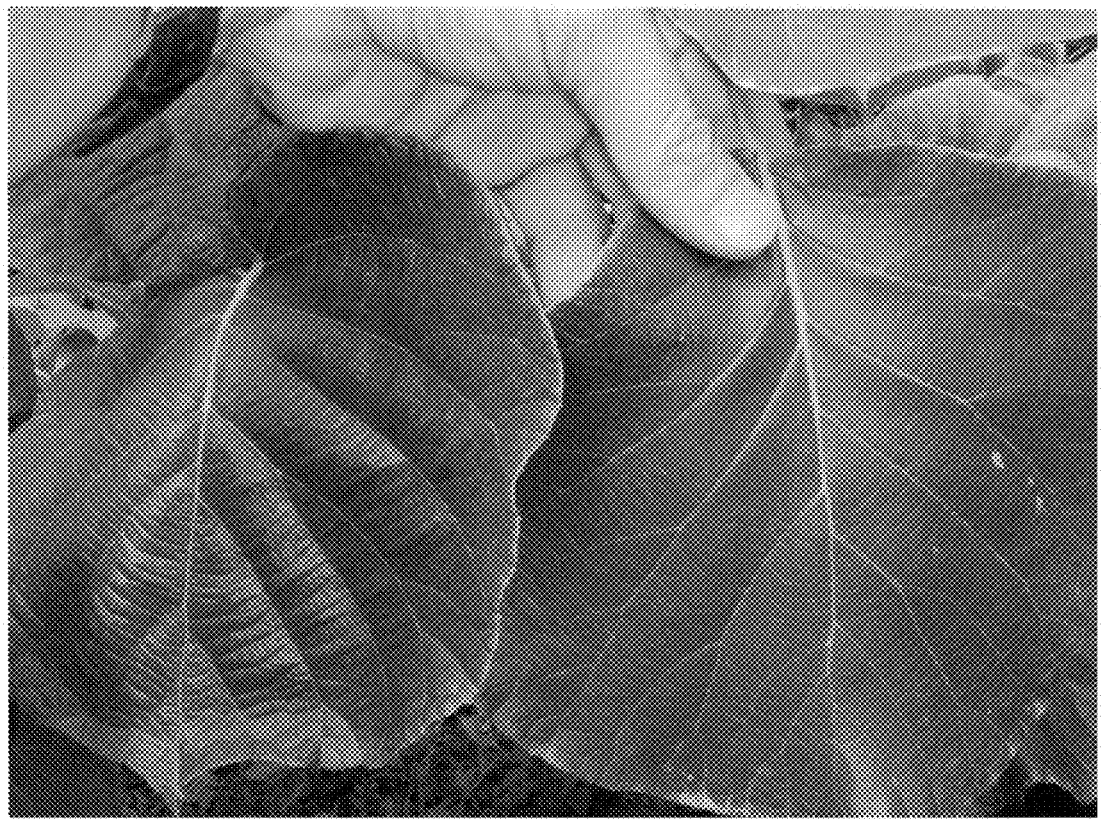
FIG. 5 is a photograph of a mature leaf of the new kiwifruit variety 'Y374'.

The mature leaf is broad ovate in shape, smooth and glossy in surface, with a mostly rounded leaf tip (FIG. 5) and typically averages approximately 210 mm in length and approximately 240 mm in width. The leaf bases are free. The petiole length averages approximately 80 mm to approximately 105 mm, is smooth in surface, and is light Yellow-green (RHS 144D). There is medium anthocyanin coloration on the upper side of the petiole. The color of the leaf blade is Medium green (RHS 138A) on the upper surface and Light green (RHS 138C) on the lower surface. There are no leaf spines. The young shoot has a smooth surface texture and is light Yellow-green (RHS 145A).

INFLORESCENCE

The number of flowers in each inflorescence is typically between one to three flowers. The average size of a flower bud is 12 mm in diameter with a round shape and light Greyed-green and White in color (RHS 196A and 155D). The pedicel length averages approximately 37.4 mm, is smooth in surface, and is light Yellow-green (RHS 144D). The sepals are medium Greyed-green (RHS 194B) to light Greyed-green (RHS 196A) in color and have an average size of about 8 mm by about 4 mm. The mean number of petals per flower is approximately 7; the mean number of pistils is 1; and the mean number of stamen is 61. The petals are arranged overlapping, and are medium Yellow (RHS 11C) when fully open. The color of the filaments is light Green (RHS 142C); the color of the anthers is medium Greyed-orange (RHS 163A); and the color of the styles is White (RHS 155D).

FRUIT

Figure 1:
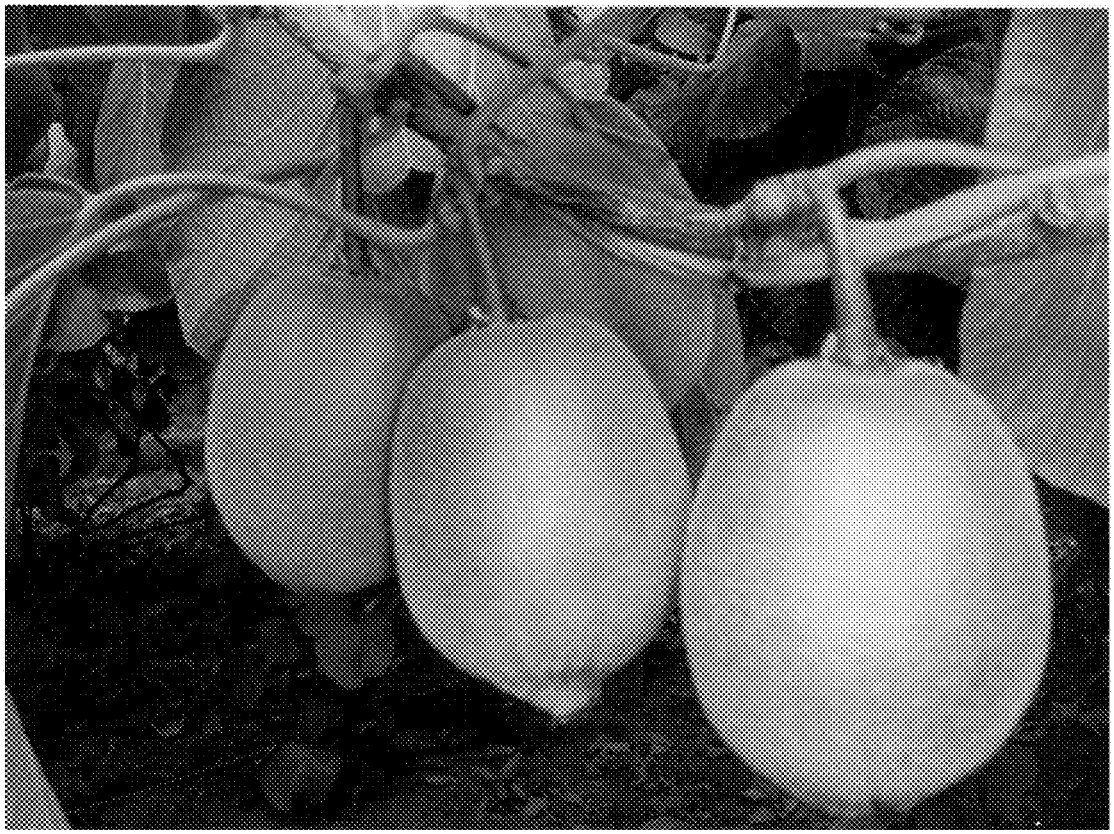
FIG. 1 is a photograph of the fruit of the new kiwifruit variety 'Y374'.
Figure 2A:
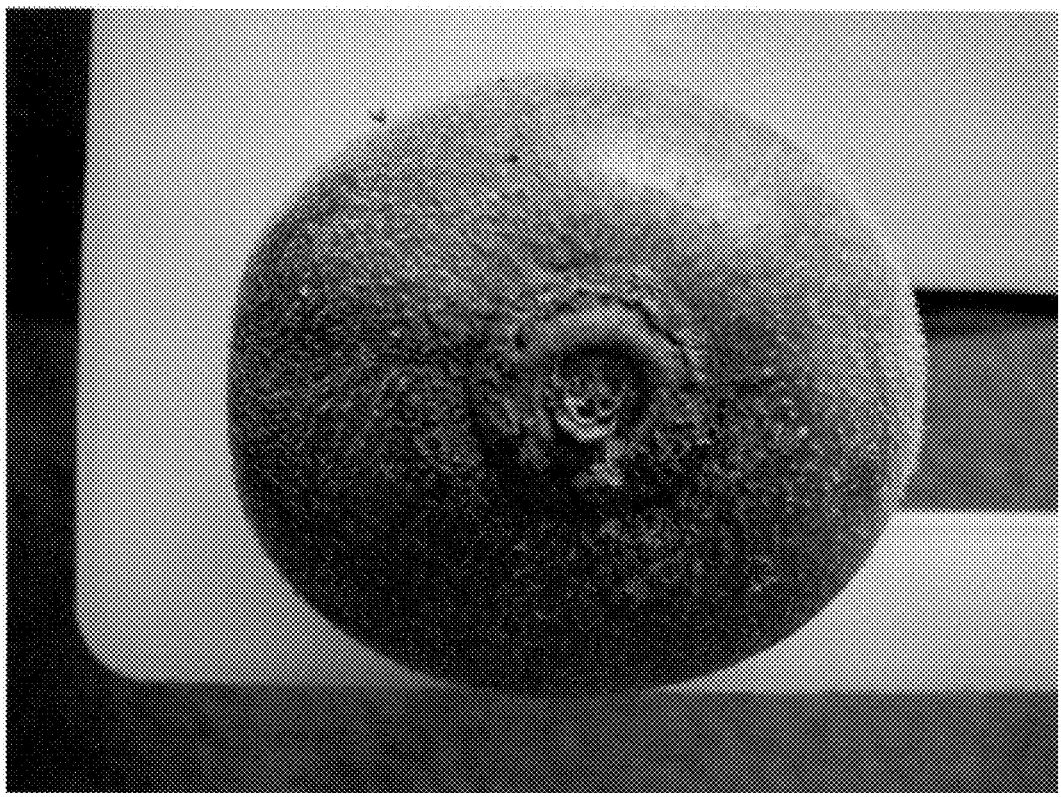
FIG. 2A is a photograph of the stem view of fruit of the variety 'Y374'.
Figure 2B:
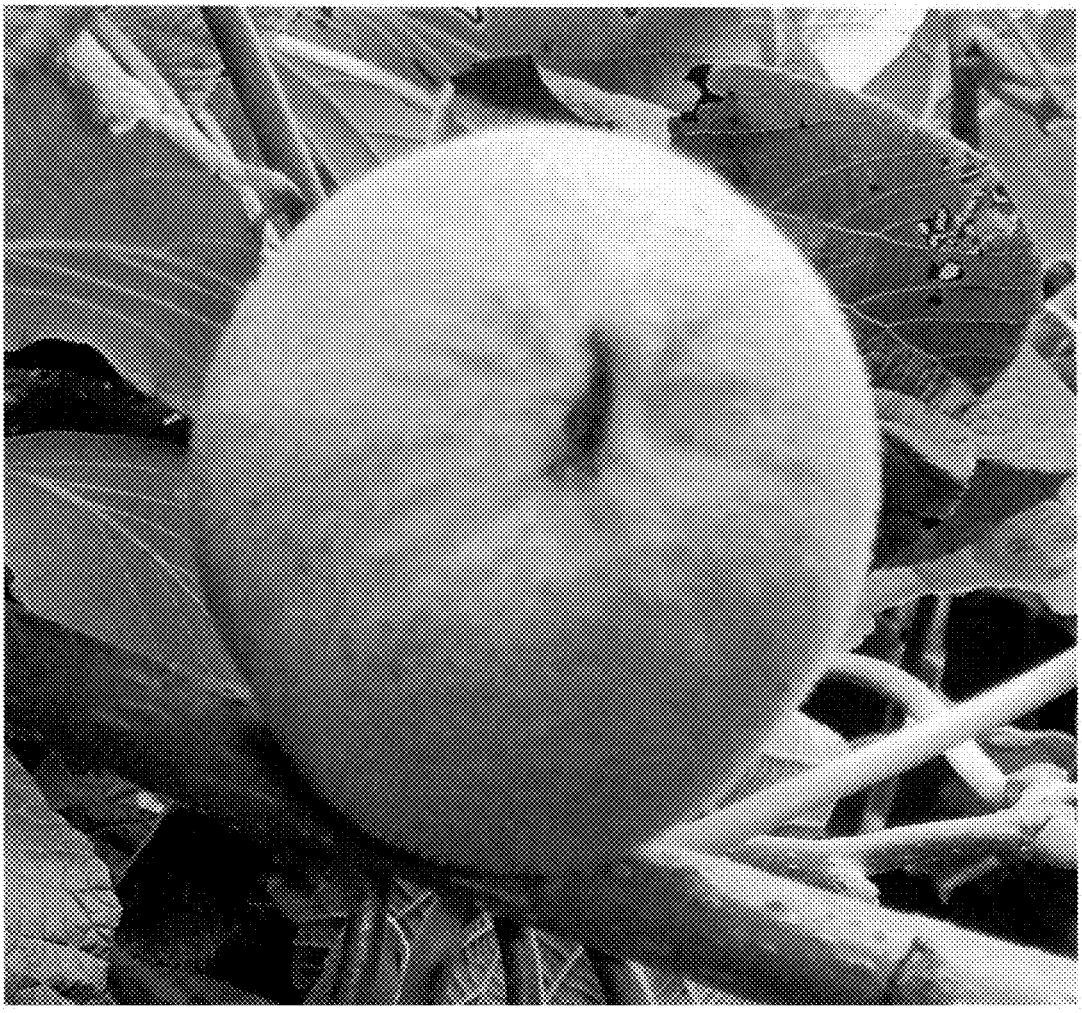
FIG. 2B is a photograph of the stylar end view of fruit of the variety 'Y374'.
Figure 3:
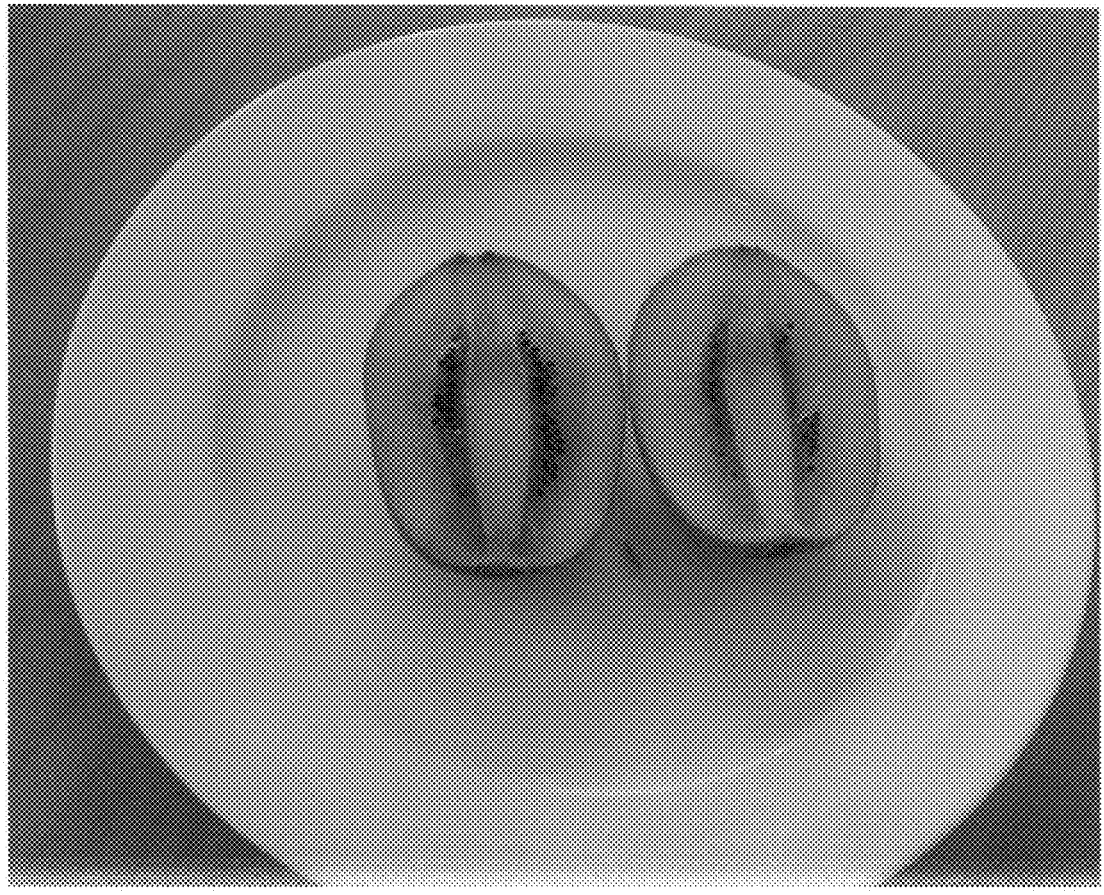
FIG. 3 is a photograph of the fruit of the new kiwifruit variety 'Y374' fruit in longitudinal-section revealing the medium-yellow pigmentation of the fruit at maturity for consumption.
Figure 4:
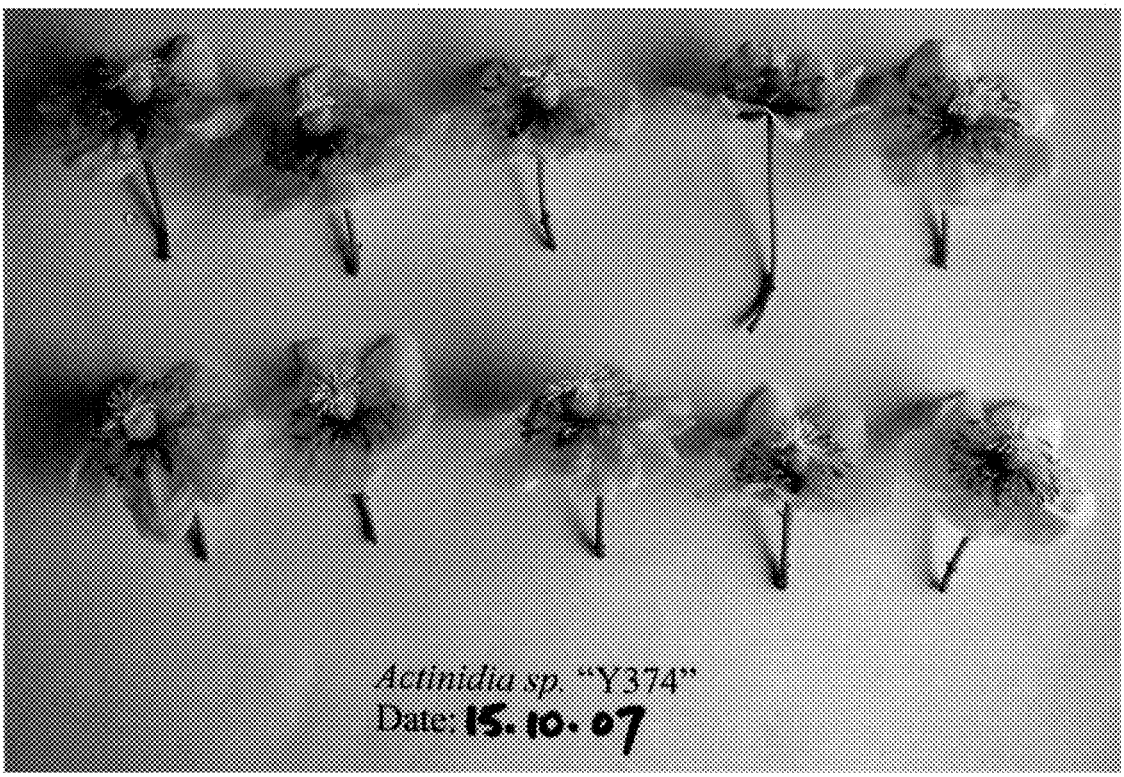
FIG. 4 is a photograph of the flowers of the new kiwifruit variety 'Y374'.

The fruit are overall large in size, averaging approximately 129 g in weight. The fruit's dimensions average approximately 70 mm in length and approximately 65 mm maximum width, with a core diameter averaging approximately 13 mm in a first direction and 5 mm along a second direction perpendicular to the first direction. The general fruit shape in longitudinal section is obovoid, with the general shape of the fruit stem end being rounded (FIG. 2A), and with the general shape of the stylar end also being rounded (FIGS. 1 and 2B). The calyx ring is strongly expressed.

The fruit skin has few fruit hairs and no lenticels. The fruit skin is medium Yellow-green in color (RHS 146C) and has average to lesser adherence of skin to flesh. The inner pericarp is colored medium Yellow (RHS 4C) at maturity for consumption. The fruit average approximately 16% Brix at maturity for consumption. The average size of the fruit core is about 15 mm by about 70 mm and is White (RHS 155C) in color.

CULTIVATION

Vegetative bud break typically occurs in early September with flowering commencing in early October. The fruit attain maturity for harvest in approximately early March. All observations made under growing conditions at Ranigiriri, New Zealand on plants 5 years in age. No plant/fruit disease or pest resistance/susceptibility has been observed. The plant has been observed to grow well in temperatures that reach 35 degrees Celsius in summers and minus 5 degrees Celsius in winters.

I claim:

1. A new and distinct variety of kiwifruit plant, substantially as herein described and illustrated.

* * * * *